(12) United States Patent
Huberman et al.

(10) Patent No.: US 7,183,106 B1
(45) Date of Patent: Feb. 27, 2007

(54) BACTERIAL INOSINE 5'-MONOPHOSPHATE DEHYDROGENASE ("IMPDH") DNA AS A DOMINANT SELECTABLE MARKER IN MAMMALS AND OTHER EUKARYOTES

(75) Inventors: Eliezer Huberman, Chicago, IL (US); Mekhine J. Baccam, Woodridge, IL (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 334 days.

(21) Appl. No.: 10/856,409

(22) Filed: May 28, 2004

(51) Int. Cl.
   *C12N 15/00* (2006.01)
(52) U.S. Cl. .................................. 435/320.1
(58) Field of Classification Search .............. 536/23.1; 435/320.1, 252.3
   See application file for complete search history.

(56) References Cited

U.S. PATENT DOCUMENTS 6,153,398 A * 11/2000 Collart et al. ................. 435/26
6,479,628 B1   11/2002 Collart et al.
2005/0202520 A1 * 9/2005 Dorn et al. .................... 435/25

OTHER PUBLICATIONS

Mekhine Baccam et al. *Bacterial IMPDH Geme Used for Selection of Mammalian Cell Transfectants*. BioTechniques. 34:1220-1230 (Jun. 2003).

* cited by examiner

*Primary Examiner*—Mark Navarro
(74) *Attorney, Agent, or Firm*—Michael J. Dobbs; Brian J. Lally; Paul A. Gottlieb

(57) ABSTRACT

The present invention relates to a nucleic acid sequence and its corresponding protein sequence useful as a dominant selectable marker in eukaryotes. More specifically the invention relates to a nucleic acid encoding a bacterial IMPDH gene that has been engineered into a eukaryotic expression vectors, thereby permitting bacterial IMPDH expression in mammalian cells. Bacterial IMPDH expression confers resistance to MPA which can be used as dominant selectable marker in eukaryotes including mammals. The invention also relates to expression vectors and cells that express the bacterial IMPDH gene as well as gene therapies and protein synthesis.

19 Claims, 4 Drawing Sheets

BACTERIAL INOSINE 5'-MONOPHOSPHATE DEHYDROGENASE ("IMPDH") DNA AS A DOMINANT SELECTABLE MARKER IN MAMMALS AND OTHER EUKARYOTES

1. U.S. GOVERNMENT RIGHTS

The United States Government has rights in this invention pursuant to Contract No. W-31-109-ENG-38 between the U.S. Department of Energy and the University of Chicago, representing Argonne National Laboratory.

2. TECHNICAL FIELD

The present invention relates to a nucleic acid sequence and its corresponding protein sequence useful as a dominant selectable marker "DSM" in eukaryotes. More specifically the invention relates to a nucleic acid encoding the bacterial IMPDH gene that has been engineered into eukaryotic expression vectors, thereby permitting bacterial Inosine 5'-monophosphate dehydrogenase "IMPDH" expression in mammalian cells. Bacterial IMPDH expression confers resistance to mycophenolic acid "MPA" which can be used as a dominant selectable marker in eukaryotes including mammals.

3. SEQUENCE LISTINGS

The electronic readable copy and paper copy of the sequence listings for this invention are identical.

4. BACKGROUND OF INVENTION

Selectable markers are genes that impart a unique characteristic to transfected organisms which is evident during a biochemical or chemical assay. For example, some selectable markers confer (upon cells transfected with the marker) a unique resistance to cytoxic agents such as antibiotics. When a selectable marker is combined with other exogenic genes (or cDNA), the marker's conferred characteristic (i.e. antibiotic resistance) can be used to identify and select the genetically altered cells from a mixed population. This ability makes selectable markers an important tool in the study and manipulation of genes. A variety of such markers have been identified and are currently in use. (See, Wei, K., and B. E. Huber. 1996. Cytosine deaminase gene as a positive selection marker. J Biol Chem. 271(7):3812–61; Baumann, R. P., D. H. Sherman, and A. C. Sartorelli. 2002. Novel selection marker for mammalian cell transfection. Biotechniques. 32(5):1030–36; Eglitis, M. A. 1991. Positive selectable markers for use with mammalian cells in culture. Hum Gene Ther. 2(3):195–201.)

However, not all genetic markers are appropriate for all cell types or experimental systems, nor are they necessarily simple and easy to use. For example, thymidine kinase requires the use or generation of cells deficient in this enzyme. (See, Wigler, M., S. Silverstein, L. S. Lee, A. Pellicer, Y. Cheng, and R. Axel. 1977. Transfer of purified herpes virus thymidine kinase gene to cultured mouse cells. Cell. 11(1):223–32.) Others markers may not be easily expressed in certain cell types or may require unique media. Some cell types may exhibit an innate resistance to the selecting drug.

The most commonly used DSM is the bacterial aminoglycoside phosphotransferase II gene (commonly referred to as the "neomycin-resistant" or "neo" gene), which confers resistance to the cytotoxic effect of the aminoglycoside antibiotic G418. (See, Southern, P. J., and P. Berg. 1982. Transformation of mammalian cells to antibiotic resistance with a bacterial gene under control of the SV40 early region promoter. J Mol Appl Genet. 1(4):327–41.) However, the high cost for G418 makes the neo gene marker less ideal for high throughput protocols. In addition, G418 causes mammalian cells to release GPI-anchored proteins making it unsuitable for the study of these proteins. (Kung, M., B. Stadelmann, U. Brodbeck, and P. Butikofer. 1997. Addition of G418 and other aminoglycoside antibiotics to mammalian cells results in the release of GPI-anchored proteins. FEBS Lett. 409(3):333–8.) A need exists for a DSM which can be used in a variety of mammalian cells which is both easy to use and is cost effective.

The present invention identifies a novel DSM, bacterial Inosine 5'-monophosphate dehydrogenase (IMPDH), which can be used for stable transfection of mammalian cells. The advantages of the present selectable marker over existing markers include the simplicity of its selection protocol, its ability to be transfected and expressed in a variety of mammalian cell types, and the cost-effectiveness of its selection drug mycophenolic acid (MPA) relative to G418 making it suitable for high throughput screenings.

IMPDH catalyzes the oxidation of IMP to XMP (xanthosine 5'-monophosphate), which is the rate-limiting step in the de novo guanine nucleotide biosynthesis pathway, and as a result is essential for the growth and proliferation of every cell. (See, Antonino, L. C., K. Straub, and J. C. Wu. 1994. Probing the active site of human IMP dehydrogenase using halogenated purine riboside 5'-monophosphates and covalent modification reagents. Biochemistry. 33(7):1760–5; Hedstrom, L. 1999. IMP dehydrogenase: mechanism of action and inhibition. Curr Med Chem. 6(7):545–60.)

Although IMPDH is evolutionarily conserved, the bacterial enzyme is orders of magnitude more resistant than mammalian IMPDH to the toxic effect of MPA. (See, Collart, F. R., J. Osipiuk, J. Trent, G. J. Olsen, and E. Huberman. 1996a. Cloning, characterization and sequence comparison of the gene coding for IMP dehydrogenase from *Pyrococcus furiosus*. Gene. 174(2):209–16; Collart, F. R., J. Osipiuk, J. Trent, G. J. Olsen, and E. Huberman. 1996b. Cloning and characterization of the gene encoding IMP dehydrogenase from *Arabidopsis thaliana*. Gene. 174(2): 217–20; Hager, P. W., F. R. Collart, E. Huberman, and B. S. Mitchell. 1995. Recombinant human inosine monophosphate dehydrogenase type I and type II proteins. Purification and characterization of inhibitor binding. Biochem Pharmacol. 49(9):1323–9; Kerr, K. M., and L. Hedstrom. 1997. The roles of conserved carboxylate residues in IMP dehydrogenase and identification of a transition state analog. Biochemistry. 36(43):13365–73; Zhou, X., M. Cahoon, P. Rosa, and L. Hedstrom. 1997. Expression, purification, and characterization of inosine 5'-monophosphate dehydrogenase from *Borrelia burgdorferi*. J Biol Chem. 272(35):21977–81; Zhang, R., G. Evans, F. J. Rotella, E. M. Westbrook, D. Beno, E. Huberman, A. Joachimiak, and F. R. Collart. 1999. Characteristics and crystal structure of bacterial inosine-5'-monophosphate dehydrogenase. Biochemistry. 38(15):4691–700.)

Based on this property, the inventors have demonstrated that expression of bacterial IMPDH in mammalian cells confers in them resistance to MPA toxicity and moreover that this enzyme is a useful DSM for the expression and selection of exogenous genes or cDNAs in mammalian cell transfections.

5. SUMMARY OF THE INVENTION

One embodiment of the invention relates to utilizing a bacterial IMPDH gene as a dominant selectable marker.

Another embodiment of the present invention relates to the insertion of bacterial IMPDH DNA into a eukaryotic (preferably a mammalian) expression vector, wherein the bacterial IMPDH DNA sequence is functionally positioned in the eukaryotic expression vector as to be expressed in a eukaryotic host cell.

A specific embodiment of the present invention relates to the insertion of a bacterial IMPDH polynucleotide into the mammalian expression vector pFLAG-CMV-2.

Another specific embodiment of the invention provides a method of producing bacterial IMPDH which comprises incorporating the nucleic acid having the sequence in (SEQ ID NO: 1) into an expression vector, transfecting a host cell with the vector and culturing the transformed host cell under conditions which result in expression of the gene.

One embodiment of the invention provides a method for using IMPDH as a resistance marker for transformation of genes into eukaryotic cells.

A specific embodiment of the present invention relates to a positive selection system the method comprising: (1) introducing into a mammalian cell, a DNA expression construct comprising the isolated bacterial IMPDH nucleic acid as set forth in SEQ ID NO: 1 growing the mammalian cell under conditions conducive to expression of bacterial IMPDH in the presence of MPA or a related analog of MPA for a time and at a concentration that is toxic to eukaryotic cells not expressing the bacterial IMPDH nucleic acid sequence, thereby allowing the mammalian cells that contain the bacterial IMPDH nucleic acid to be identified (3) selecting IMPDH expressing cells which are resistant to MPA or related MPA analogs.

In accordance with one embodiment of the invention there is provided a mammalian expression construct comprising the IMPDH nucleic acid complement thereof, a degenerate variant thereof, wherein the IMPDH nucleic acid sequence (SEQ ID NO: 1) is operably linked in either the 5' or 3' end, or at both ends to the regulatory sequence(s) such that the transcription and/or translation of the IMPDH gene is regulated by these sequences.

Another embodiment of the present invention relates to the creation of a double positive selection system, wherein the double positive expression is created by the insertion of a polynucleotide encoding bacterial IMPDH and another positive selection marker DNA into a eukaryotic (preferably a mammalian) expression vector or other expression construct, wherein the inserted nucleic acid sequences are functionally positioned in the eukaryotic expression vector as to be expressed in a eukaryotic host cell.

A specific embodiment of the present invention relates to a double positive expression vector created by the insertion of bacterial IMPDH DNA into the mammalian expression vector pIRES2-EGFP, wherein the inserted DNA is functionally positioned in the expression vector as to be expressed in a mammalian host.

The scope of the present invention is not meant to be limited to the exact sequence of the nucleotide sequences set forth in (SEQ ID NO: 1) or the use thereof. The invention contemplates certain modifications to the sequence, including deletions, insertions, and substitutions, that are well known to those skilled in the art. For example, the invention contemplates modifications to the sequence found in (SEQ ID NO: 1) with codons that encode amino acids that are chemically equivalent to the amino acids in the native protein. An amino acid substitution involving the substitution of an amino acid with a chemically equivalent amino acid is known as a conserved amino acid substitution.

Chemical equivalency can be determined by one or more the following characteristics: charge, size, hydrophobicity/hydrophilicity, cyclic/non-cyclic, aromatic/non-aromatic etc. For example, a codon encoding a neutral non-polar amino acid can be substituted with another codon that encodes a neutral non-polar amino acid, with a reasonable expectation of producing a biologically equivalent protein.

Amino acids can generally be classified into four groups. Acidic residues are hydrophilic and have a negative charge to loss of $H^+$ at physiological pH. Basic residues are also hydrophilic but have a positive charge to association with H+ at physiological pH. Neutral nonpolar residues are hydrophobic and are not charged at physiological pH. Neutral polar residues are hydrophilic and are not charged at physiological pH. Amino acid residues can be further classified as cyclic or noncyclic and aromatic or nonaromatic, self-explanatory classifications with respect to side chain substituent groups of the residues, and as small or large. The residue is considered small if it contains a total of 4 carbon atoms or less, inclusive of the carboxyl carbon. Small residues are always non-aromatic.

Of naturally occurring amino acids, aspartic acid and glutamic acid are acidic; arginine and lysine are basic and noncylclic; histidine is basic and cyclic; glycine, serine and cysteine are neutral, polar and small; alanine is neutral, nonpolar and small; threonine, asparagine and glutamine are neutral, polar, large and nonaromatic; tyrosine is neutral, polar, large and aromatic; valine, isoleucine, leucine and methionine are neutral, nonpolar, large and nonaromatic; and phenylalanine and tryptophan are neutral, nonpolar, large and aromatic. Proline, although technically neutral, nonpolar, large, cyclic and nonaromatic is a special case due to its known effects on secondary conformation of peptide chains, and is not, therefore included in this defined group.

There are also common amino acids which are not encoded by the genetic code include by example and not limitation: sarcosine, beta-alanine, 2,3-diamino propionic and alpha-aminisobutryric acid which are neutral, nonpolar and small; t-butylalanine, t-butylglycine, methylisoleucine, norleucine and cyclohexylalanine which are neutral, nonpolar, large and nonaromatic; ornithine which is basic and non-cylclic; cysteic acid which is acidic; citrulline, acetyl lysine and methionine sulfoxide which are neutral, polar, large and nonaromatic; and phenylglycine, 2-naphtylalanine, β2-thienylalanine and 1,2,3,4-tetrahydroisoquinoline-3-carboxylic acid which are neutral, nonpolar, large and aromatic. Other modifications are known in the art some of which are discussed in U.S. Pat. No. 6,465,237 issued to Tomlinson on Oct. 15, 2002.

The invention also contemplates other nucleic acid sequences including complements and degenerate variants of SEQ ID NO: 1 as well as sequences that selectively hybridize under stringent conditions to SEQ ID NO: 1 or variants thereof.

6. BRIEF DESCRIPTION OF THE DRAWINGS

FIG. 1A. illustrates the structure of the plasmid pFLAG-IMPDH.

FIG. 1B. illustrates the structure of the bicistronic expression vector pIMPDH-EGFP.

FIG. 1C. illustrates the structure of the bicistronic expression vector pNEO-EGFP.

FIG. 2A. illustrates the viability of human MDA-MB 231 cells with and without incorporation of the bacterial IMPDH gene when grown in varying amounts of MPA.

FIG. 2B. shows the viability of human PC3 cells with and without incorporation of the bacterial IMPDH gene when grown in varying amounts of MPA.

FIG. 2C. shows the viability of monkey COS7 cells with and without incorporation of the bacterial IMPDH gene when grown in varying amounts of MPA.

FIG. 2D. shows the viability of Chinese hamster V79 cells with and without incorporation of the bacterial IMPDH gene when grown in varying amounts of MPA.

FIG. 3A. is a histogram of GFP expression in pooled MPA-resistant colonies from V79 cells co-transfected with pFLAG-IMPDH and pHygEGFP vectors.

the shaded histograms in 3A, B and C represent V79 cells transfected with the pFLAG-IMPDH vector only.

Figure 4A:
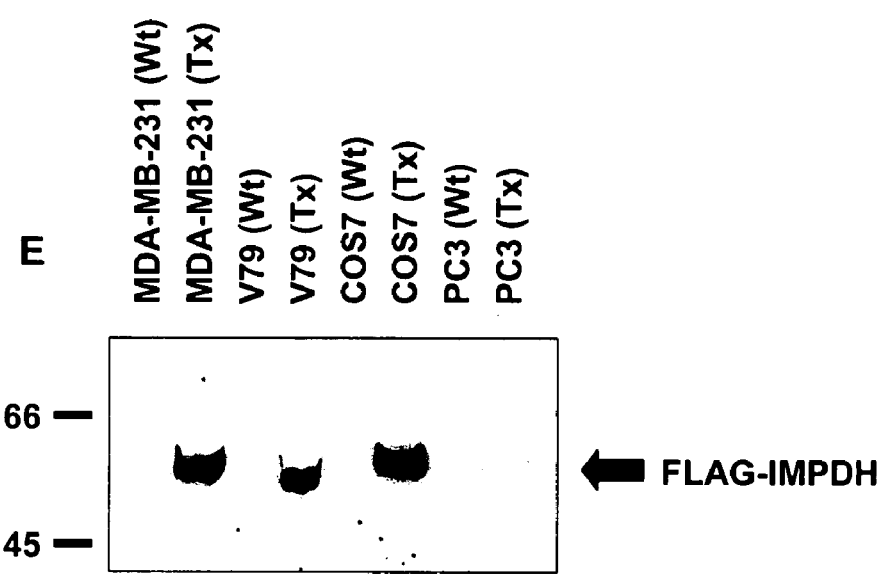

FIG. 4A. shows Western blot analysis performed with an anti-FLAG antibody and developed by enhanced chemiluminescence to detect FLAG-tagged E. coli IMPDH Whole cell lysates ($1 \times 10^5$ cell equivalence) of control (not transfected parental) (Wt) or IMPDH-transfected (Tx) cells were subjected to SDS-PAGE and Western blot analysis.

Figure 4B:

FIG. 4B is a 2 h over-exposure of the Western blot presented in FIG. 4A. Results are representative of three similar experiments and three different cultures of each transfectant.

7. DEFINITIONS

Before proceeding further with a description of the specific embodiments of the present invention, a number of terms will be defined.

As used herein, a compound or molecule is an organic or inorganic assembly of atoms of any size, and can include macromolecules, peptides, polypeptides, whole proteins, and polynucleotides.

As used herein, a polynucleotide is a nucleic acid of more than one nucleotide. A polynucleotide can be made up of multiple poly-nucleotide units that are referred to be a description of the unit. For example, a polynucleotide can comprise within its bounds a polynucleotide(s) having a coding sequence(s), a polynucleotide(s) that is a regulatory region(s) and/or other polynucleotide units commonly used in the art.

A polypeptide is a series of amino acids linked together by peptide bonds.

An isolated nucleic acid will be nucleic acid that is identified and separated from contaminant nucleic acids. The nucleic acid may be labeled for diagnostic and probe purposes, using any label known and described in the art as useful in connection with diagnostic assays. The isolated nucleic acid molecule of the present invention can include a deoxyribonucleic acid molecule (DNA), such as genomic DNA and complementary cDNA which can be single (coding or noncoding strand) or double stranded, as well as synthetic DNA, such as synthesized single stranded polynucleotide. The isolated nucleic acid molecule of the present invention can also include a ribonucleic acid molecule (RNA).

The determination of percent identity or homology between two sequences is accomplished using the algorithm of Karlin and Altschul (1990) Proc. Nat'l Acad. Sci. USA 87: 2264–2268, modified as in Karlin and Altschul (1993) Proc. Nat'l Acad. Sci. USA 90:5873–5877. Such an algorithm is incorporated into the NBLAST and XBLAST programs of Altschul et al. (1990) J. Mol. Biol. 215:403–410. BLAST nucleotide searches are performed with the NBLAST program, score=100, wordlength=12 to obtain nucleotide sequences homologous to the nucleic acid molecules of the invention. BLAST protein searches are performed with the XBLAST program, score=50, wordlength=3 to obtain amino acid sequences homologous to the protein molecules of the invention. To obtain gapped alignments for comparison purposes, Gapped BLAST is utilized as described in Altschul et al. (1997) Nucleic Acids Res. 25: 3389–3402. When utilizing BLAST and Gapped BLAST programs, the default parameters of the respective programs (e.g., XBLAST and NBLAST) are used. See the website for the National Center for Biological Information As used herein, the terms hybridization (hybridizing) and specificity (specific for) in the context of nucleotide sequences are used interchangeably. The ability of two nucleotide sequences to hybridize to each other is based upon a degree of complementarity of the two nucleotide sequences, which in turn is based on the fraction of matched complementary nucleotide pairs. The more nucleotides in a given sequence that are complementary to another sequence, the greater the degree of hybridization of one to the other. The degree of hybridization also depends on the conditions of stringency which include: temperature, solvent ratios, salt concentrations, and the like.

In particular, selective hybridization pertains to conditions in which the degree of hybridization of a polynucleotide of the invention to its target would require complete or nearly complete complementarity. The complementarity must be sufficiently high as to assure that the polynucleotide of the invention will bind specifically to the target relative to binding other nucleic acids present in the hybridization medium. With selective hybridization, complementarity will be 90–100%, preferably 95–100%, more preferably 100%.

The term stringent conditions is known in the art from standard protocols (e.g. Current Protocols in Molecular Biology, editors F. Ausubel et al., John Wiley and Sons, Inc. 1994) and is when hybridization to a filter-bound DNA in 0.5M $NaHPO_4$ (pH7.2), 7% sodium dodecyl sulfate (SDS), 1 mM EDTA at +65° C.

Degenerate variant is the redundancy or degeneracy of the genetic code as is well known in the art. Because the genetic code is degenerate, more than one codon may be used to encode a particular amino acid, and therefore, the amino acid sequence can be encoded by any set of similar DNA oligonucleotides. With respect to nucleotides, therefore, the term degenerate variant is also intended to encompass those DNA sequences that contain alternative codons which code for the eventual translation of the identical amino acid.

The term operably linked refers to construction where the components are positioned in a way to permit them to function in their intended manner vis-à-vis each other. A transcription control sequence operably linked to a coding sequence refers to a control sequence capable of effecting the transcription of the coding sequence.

Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in a recombinant cell useful for the expression of bacterial IMPDH, and/or useful to administer to a mammal in the method of the present invention. A variety of such transcription control sequences are known to those skilled in the art. Transcription control sequences include those which function in mammalian, bacterial, or insect cells, and preferably in mammalian cells. A list of transcription control sequences include, but are not limited to, simian virus 40 (SV-40), .beta.-actin, retroviral long terminal repeat (LTR), Rous sarcoma virus (RSV), cytomegalovirus (CMV), tac, lac, trp, trc, oxy-pro, omp/lpp, rrnB, bacteriophage lambda (.lambda.) (such as .lambda.p-.sub.L and .lambda.p.sub.R and fusions that include such promoters), bacteriophage T7, T7 lac, bacteriophage T3, bacteriophage SP6, bacteriophage S01, metallothionein, alpha mating factor, *Pichia* alcohol oxidase, alphavirus subgenomic promoters (such as Sindbis virus subgenomic promoters), baculovirus, *Heliothis zea* insect virus, vaccinia virus and other poxviruses, herpesvirus, and adenovirus transcription control sequences, as well as other sequences capable of controlling gene expression in eukaryotic cells. Additional suitable transcription control sequences include tissue-specific promoters and enhancers (e.g., T cell-specific enhancers and promoters). Transcription control sequences of the present invention can also include naturally occurring transcription control sequences naturally associated with a gene encoding a bacterial IMPDH gene useful in a method of the present invention.

The term expression vector includes a variety of vectors capable of introducing exogenic nucleic acid into a host organism for expression. Expression vectors include but are not limited to plasmids, cosmids, phagemids, artificial chromosomes (YACs) or modified viruses, however, the vector must be compatible with the host organism. The control sequences may be supplied by the gene to be expressed or by the expression vector. The expression vector may contain unique or conveniently located restriction sites to allow severing and/or rearranging portions of the DNA inserts in an expression vector.

8. GENERAL DESCRIPTION OF METHODS AND RESULTS

The present invention relates to a dominant selectable marker ("DSM"). Dominant selective markers act as a selection tools to identify cells that have been successfully transfected to express exogenous genes or cDNAs in eukaryotic cells. More specifically the present invention describes a simple and versatile DSM that involves bacterial IMP dehydrogenase ("IMPDH"), an enzyme essential for the replication of mammalian and bacterial cells. Although IMPDH is evolutionarily conserved, the bacterial enzyme is orders of magnitude more resistant to the toxic effect of the drug, mycophenolic acid ("MPA"). The transfection of human, monkey or Chinese hamster cell lines with an expression vector containing bacterial IMPDH and MPA treatment resulted in the selection of colonies with a strikingly increased resistance to MPA toxicity. Analysis of cells derived from these colonies indicated that the acquisition of this resistance was associated with bacterial IMPDH protein expression. As a proof of principle, it was shown that mammalian cell transfection with a bicistronic IMPDH/green fluorescent protein expression vector and MPA treatment can be used to successfully select transfectants that express the fluorescent protein. These results indicate that bacterial IMPDH is a practical DSM that can be used for the selection of transfectants that express exogenous genes or cDNAs in a variety of mammalian cells. The bacterial IMPDH gene could also be useful in a variety of other applications including but not limited to: gene therapy and drug design, development and selection.

8.1 Construction, Transfection and Expression IMPDH Expression Vector

Figure 1A:
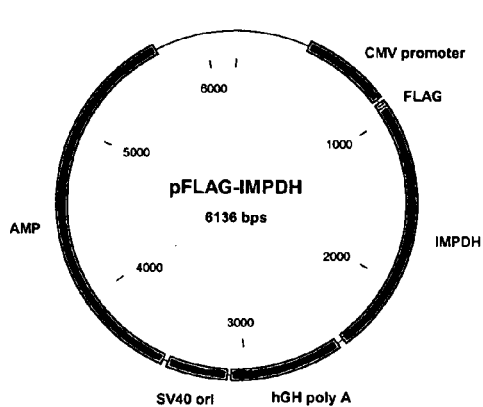

To determine the suitability of bacterial IMPDH as a DSM for the selection of mammalian cell transfectants, a vector containing FLAG epitope-tagged *E. coli* IMPDH under the control of the CMV promoter was constructed (FIG. 1A). Transfection of Chinese hamster V79, human MDA-MB-231 and PC3, and monkey COS7 cells with this vector and incubation for 10–20 d with 0.8 µg/ml of MPA yielded MPA-resistant colonies in the four cell types. Transfection efficiencies of the various cell types as measured by the number of MPA-resistant colonies per $1 \times 10^6$ viable electroporated cells are tabulated in Table 1, experiment 1. No such colonies were obtained after transfection with the same vector but without the IMPDH gene. Although, the pFLAG-CMV-2-vector was used, those knowledgeable in the art could envision various other eukaryotic (preferably mammalian) expression vectors and constructs that could also be utilized in conjunction with the present invention. These vectors and constructs include but are not limited to: pCI mammalian expression vector (Promega, Madison, Wis.), pSI mammalian expression vector (Promega, Madison, Wis.), pRK-5-C-GFP and pRK-5-N-GFP mammalian expression vectors (BD Pharmingen, San Diego, Calif.), Vitality hrGFPII-1 mammalian expression vector (Stratagene, La Jolla, Calif.), LRCX retroviral vectors (BD Biosciences Clontech, Palo Alto, Calif.), pTracer-CMV-2 vector (Invitrogen, Carlsbad, Calif.) pCDNA expression vectors (Invitrogen, Carlsbad, Calif.), pCEP4 episomal mammalian expression vector (Invitrogen, Carlsbad, Calif.), pDisplay vector (Invitrogen, Carlsbad, Calif.).

TABLE 1

| | Transfection Efficiency | | |
|---|---|---|---|
| | Cell type | Vector | Colonies per $1 \times 10^8$ viable cells |
| Experiment 1* | V79 | pFLAG-IMPDH | 150 |
| | MDA-MB-231 | pFLAG-IMPDH | 14 |
| | PC3 | pFLAG-IMPDH | 6 |
| | COS7 | pFLAG-IMPDH | 30 |
| Experiment 2 | V79 | pIMPDH-EGFP | 78 |
| | MDA-MB-231 | pIMPDH-EGFP | 22 |
| | PC3 | pIMPDH-EGFP | 9 |
| Experiment 3 | V79 | pIMPDH-EGFP | 400 |
| | V79 | pNEO-EGFP | 620 |

*Transfection with a control vector that does not contain the IMPDH gene failed to yield any colonies per $3 \times 10^6$ tested viable control transfected cells.

Figure 2A:
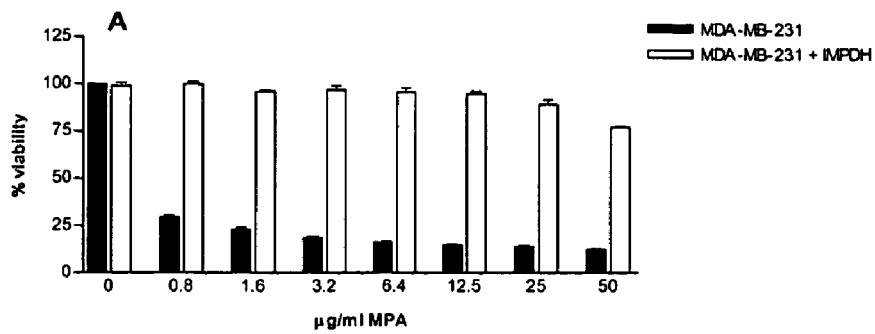
Figure 2B:
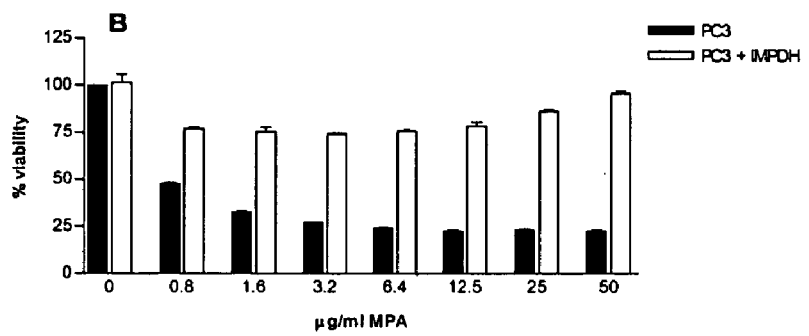

To further substantiate their resistance, 7 individual MPA-resistant V79 colonies were isolated and verified, by means of the MTT assay, that their cells were resistant to the cytotoxic effect of up to 50 µg/ml MPA. In contrast, the parental cells failed to grow in the presence of as little as 0.8 µg/ml of the drug. In addition, single cell-derived cultures were established from pooled MPA-resistant colonies from each of the four cell types and determined their susceptibility to different concentrations of MPA. The results indicated that these cells too exhibited resistance to the cytotoxic effect of up to 50 µg/ml MPA. (FIGS. 2A, B, C and D).

Figure 2C:
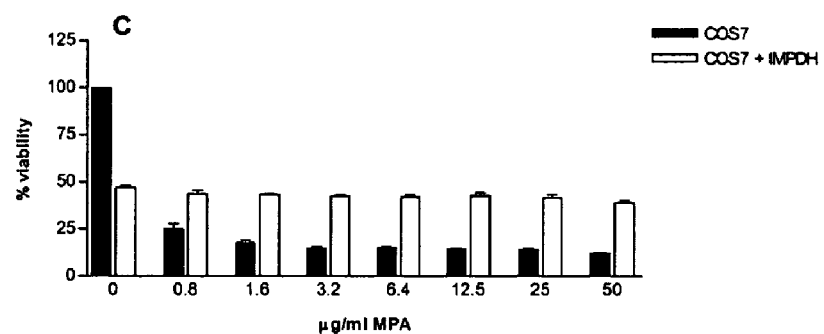
Figure 2D:
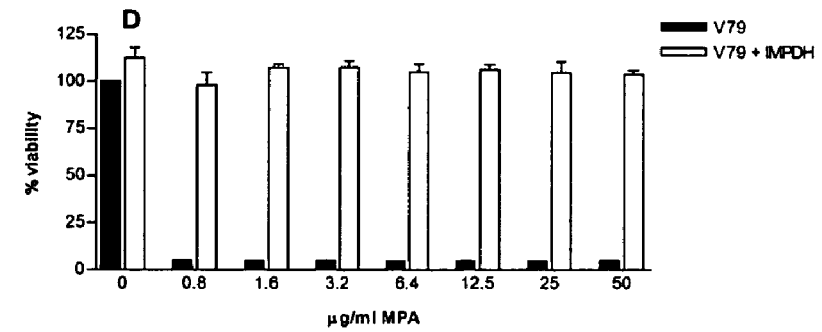

Growth inhibition of wild type V79 cells, which have a doubling time of about 12 h compared to 24 h for the other cell types, was detected as early as 3 d after MPA treatment compared to 6 d for MDA-MB-231, PC3 and COS7 cells. Although on the $6^{th}$ day after MPA treatment there was some MTT staining in control (not transfected parental) cultures (FIGS. 2A, B and C), no replicating cells were observed. Moreover, after 4 weeks of this treatment these control cultures exhibited no MTT staining above background levels (data not shown). Unlike the other cell types, the MPA-resistant COS7 cells did not proliferate as vigorously as the wild type cells (FIG. 2C).

Next, it was determined whether MPA-resistant cells expressed the transfected bacterial IMPDH protein. To avoid potential cross-reactivity of a bacterial IMPDH antibody with the resident mammalian enzyme and to facilitate the detection of the protein, a vector containing FLAG epitope-tagged E. coli IMPDH was constructed (FIG. 1A). Western blot analysis with an anti-FLAG antibody indicated that cells from MPA-resistant colonies but not wild type cells contain an antigenic protein band with a molecular mass of 53 kDa (FIG. 4), which is the predicted size of the E. coli IMPDH. (Zhang, R., G. Evans, F. J. Rotella, E. M. Westbrook, D. Beno, E. Huberman, A. Joachimiak, and F. R. Collart. 1999. Characteristics and crystal structure of bacterial inosine-5'-monophosphate dehydrogenase. Biochemistry. 38(15):4691–700.)

The band from the MPA-resistant PC3 cells required a longer exposure time due to a lower level of bacterial IMPDH expression (FIG. 4, lower panel). Based on these results, it was concluded that MPA resistance of pFLAG-IMPDH vector-transfected mammalian cells is coupled with bacterial IMPDH protein expression.

Figure 1B:
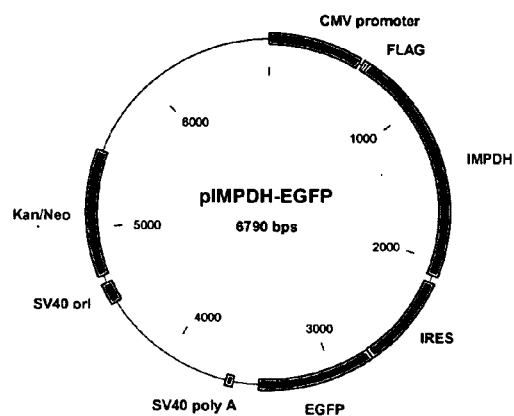
Figure 3A:
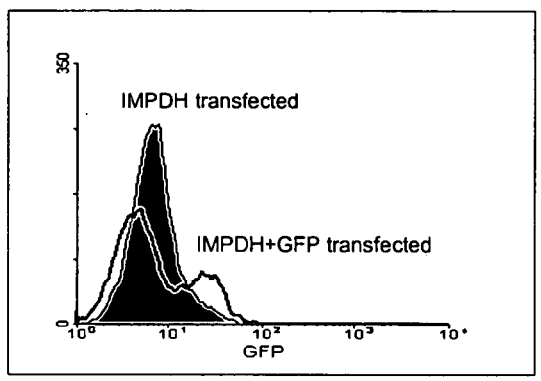
FIG. 3B is a histogram of GFP expression in MPA-resistant culture derived from single V79 cells originally transfected with the bicistronic pIMPDH-EGFP vector.
FIGS. 3C and 3D are histograms directly comparing GFP expression between (C) IMPDH and (D) NEO-EGFP vectors transfected V79 cells. The shaded histogram in (D) represent the control V79 cells not transfected.
Figure 3B:
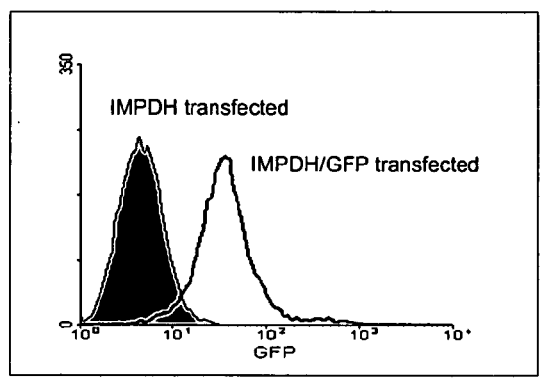

8.2 Construction, Transfection and Expression of IMPDH-EGFP and Double Positive Expression Systems Because DSMs are used to isolate mammalian cell transfectants that express an exogenous gene or cDNA of interest, it was decided to determine whether bacterial IMPDH could be used to obtain such cells. A strategy often used to select for transfectants involves co-transfection of cells with a vector containing the DSM along with another vector containing the exogenous gene or cDNA of interest. For this reason, V79 cells were contrasfected with pFLAG-IMPDH and pHygEGFP vectors and selected for transfectants in MPA-containing medium. Fluorescence microscopy and FACS analysis of cultures derived from pooled MPA-resistant colonies indicated that only about 30% of these cells express GFP (FIG. 3A). To increase the likelihood of selecting for cells expressing both bacterial IMPDH and GFP, we generated a bicistronic expression vector that contains both the bacterial IMPDH and GFP genes (FIG. 1B). Transfection of V79, MDA-MB-231 or PC3 cells with this vector and treatment with the selective agent also yielded MPA-resistant colonies. The transfection efficiencies of the various cell types are shown in Table 1, experiment 2. Microscopic observation as well as FACS analysis indicated that the MPA-resistant cells obtained from pooled colonies or from colonies derived from single cells express GFP (FIG. 3B). Moreover, when cultured for 2 months in the presence of MPA they continued to express GFP. These results indicate the usefulness of bacterial IMPDH in the selection of mammalian cell transfectants expressing an exogenous protein.

Figure 1C:
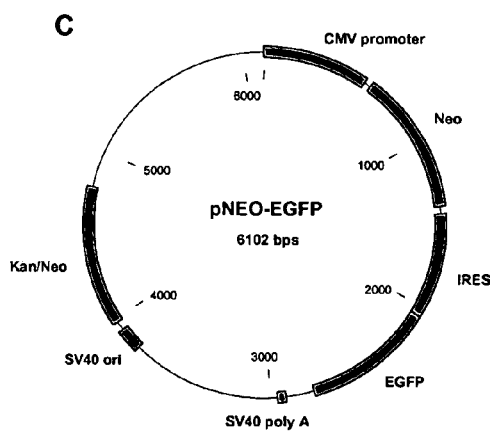
Figure 3C:
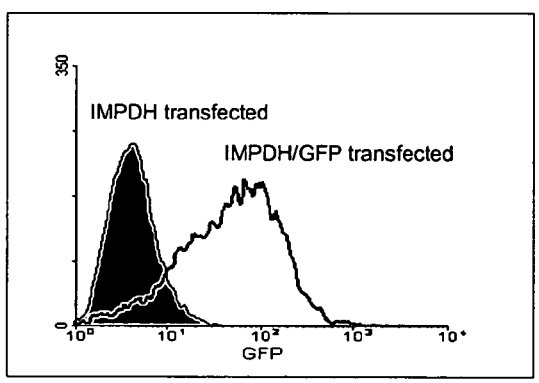
Figure 3D:
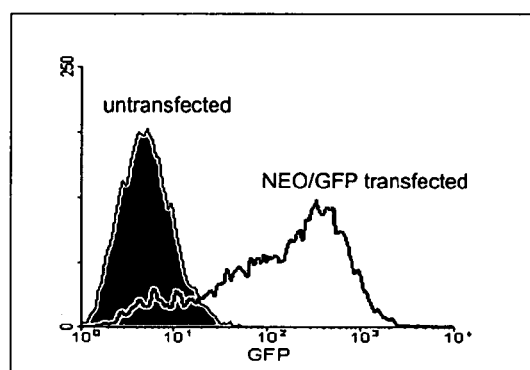

To further demonstrate the effectiveness of this gene as a DSM, the transfection efficiency of the IMPDH vector was compared to that of the commonly used DSM, namely the neo gene (FIG. 1C). Because the base vector (pIRES2-EGFP) used in this study has a neo gene outside of the bicistronic expression vector which contains the EGFP region, the pNEO-IMPDH vector was linearized with Cla I to render the aforementioned neo gene nonfunctional while keeping the NEO-IRES-EGFP bicistronic genes fully intact. As a control, the pIMPDH-EGFP vector was also linearized with the same endonuclease. Transfection with either the linearized pIMPDH-EGFP or pNEO-EGFP vector resulted in 400 MPA and 620 G418 resistant colonies per $1\times10^6$ viable transfected cells, respectively (Table 1, experiment 3). Although transfection efficiencies can vary from day to day (Table 1, experiment 2 and experiment 3, V79 cells transfected with pIMPDH-EGFP), a direct comparison of the IMPDH and NEO containing vectors indicated comparable transfection efficiencies. Expression of GFP in the MPA and G418 resistant cells was verified by FACS analysis (FIGS. 3C and D).

Although EGFP was used in the present case several a variety of other genes of interest or nucleic acid sequences (including other selectable markers) can be inserted into a bicistronic (or multi-cistronic) vector along with the bacterial IMPDH DNA. Other flurescent proteins include but are not limited to: ECFP, EYFP, and DsRed (BD Biosciences Clonetech, Palo Alto, Calif.)

8.3 Discussion of the Results

The present studies show that transfection of mammalian cells with a vector containing the bacterial IMPDH gene conferred in them a selective growth advantage in the presence of the cytotoxic drug MPA. It has also been shown that IMPDH allows for the selection of transfectants that express an exogenous gene of interest, namely GFP. The ability to express the bacterial IMPDH gene in four different mammalian cell types from three different species indicates the versatility of this DSM.

Because IMPDH is common in all living cells, we did not expect exogenously expressed bacterial IMPDH to have an adverse effect on mammalian cell function. Yet, ectopic expression of bacterial IMPDH caused the COS7 cells to grow at a somewhat slower growth rate than the parental cells (FIG. 2C). This aberrant behavior is most likely due to an interaction between the SV40 origin of replication, which is a component of our vector, and the viral T-antigen, which is expressed in these cells. Such an interaction may result in high levels of vector replication prior to its integration into the cellular genome and as a consequence lead to a high copy number of integration and aberrant cellular DNA replication. For this reason, the reduced replication of the COS7 transfectants may be unique to these cells and not be a problem with cell types which do not express the viral T-antigen, as exemplified by the other 3 cell lines tested in the present study.

MPA blocks the de novo guanine nucleotide biosynthesis pathway by inhibiting IMPDH. However, guanine nucleotides can also be synthesized via the salvage pathway by utilizing guanosine and/or guanine and the mammalian enzyme hypoxanthine-guanine phosphoribosyltransferase (HGPRT). Some batches of FBS may contain unusually high concentrations of guanosine and/or guanine, which could potentially reduce the effectiveness of the selection process. In this respect, addition of high concentrations of guanine or guanosine (100–500 μM) to the culture medium has been reported to reverse the effects of MPA. (Meredith, M., G. Li, and S. A. Metz. 1997. Inhibition of calcium-induced insulin secretion from intact HIT-T15 or INS-1 beta cells by GTP depletion. Biochem Pharmacol. 53(12):1873–82. Weigel, G., P. Bertalanffy, and E. Wolner. 2002. Depletion of intracellular GTP results in nuclear factor-kappaB activation and intercellular adhesion molecule-1 expression in human endothelial cells. Mol Pharmacol. 62(3):453–462.) However, it is unlikely that such concentrations are present in commercially available sera. Moreover, IMPDH inhibitors including MPA have been reported to also inhibit the activity of the guanine salvage pathway (Yalowitz, J. A., and H. N. Jayaram. 2000. Molecular targets of guanine nucleotides in differentiation, proliferation and apoptosis. Anticancer Res. 20(4):2329–38. Weber, G., Y. Natsumeda, and K. Pillwein. 1985. Targets and markers of selective action of tiazofurin. Adv Enzyme Regul. 24:45–65. Simili, M., C. M. Colella, M. Debatisse, and G. Buttin. 1983. Increased inhibition of HGPRT by IMP and GMP and higher levels of PRPP in an 8-azaguanine-hat resistant mutant of Chinese hamster cells. Cell Biol Int Rep. 7(2):121–8. Xu, Y., J. Eads, J. C. Sacchettini, and C. Grubmeyer. 1997. Kinetic mechanism of human hypoxanthine-guanine phosphoribosyltransferase: rapid phosphoribosyl transfer chemistry. Biochemistry. 36(12):3700–12. Ahmed, N., and M. J. Weidemann. 1995. Biochemical effect of three different inhibitors of purine/pyrimidine metabolism on differentiation in HL60 cells. Leukemia Res. 19(4):263–273.) Nevertheless, a proper dose response curve of MPA toxicity should be performed prior to using IMPDH for selection.

Although MPA has been utilized previously as a selectable agent in conjunction with the *E. coli* xanthine-guanine phosphoribosyltransferase (XGPRT) gene we feel that our system is more advantageous. Selection with IMPDH requires only MPA while selection with XGPRT necessitates MPA as well as xanthine, hypoxanthine, thymidine and aminopterin. Moreover, expression of the bacterial XGPRT protein which uses xanthine as a substrate instead of hypoxanthine, which is used by the mammalian enzyme HGPRT, could have unforeseen potential adverse effects. Interestingly, MPA-resistant wild type V79 and murine neuroblastoma cells have been reported (Huberman, E., C. K. McKeown, and J. Friedman. 1981. Mutagen-induced resistance to mycophenolic acid in hamster cells can be associated with increased inosine 5'-phosphate dehydrogenase activity. Proc Natl Acad Sci USA. 78(5):3151–4. Collart, F. R., and E. Huberman. 1987. Amplification of the IMP dehydrogenase gene in Chinese hamster cells resistant to mycophenolic acid. Mol Cell Biol. 7(9):3328–31.) Resistance in these cells, which only express endogenous mammalian IMPDH, was obtained as a resulted of IMPDH gene amplification after a prolonged and stepwise process involving the use of increased MPA concentrations. It is unlikely that a significant fraction of naturally resistant cells would be generated by our selection protocol, which uses a higher concentration of MPA and a shorter selection time than those used in the initial selection of the cells with amplified resident IMPDH. In agreement with this notion, none of the cultures transfected with control vectors generated MPA-resistant colonies.

In addition to being a new, the IMPDH DSM has several advantages over existing ones. First, unlike some other markers that require specialized medium, the present DSM can be used with a wide variety of media and the selection procedure is simple since selection only requires addition of an appropriate concentration of MPA to such a medium. Second, this DSM does not necessitate an IMPDH-deficient cell in contrast to certain selectable markers such as thymidine kinase, which requires a thymidine kinase-deficient cell. As a result, the IMPDH DSM is less time consuming to set up. Lastly, the IMPDH DSM has the potential to be used in high throughput screenings. Unlike the widely used neo DSM, which requires a high dose range (100 to 1000 μg/ml) of the expensive selection drug G418, the bacterial IMPDH DSM uses MPA at a dose range 2–3 orders of magnitude lower, thus making it a cost-effective alternative for use in various high throughput screenings.

9. MOLECULAR BIOLOGY PROTOCOLS

In practicing the present invention several conventional techniques in microbiology and molecular biology (recombinant DNA) are used. Such techniques are well known and are explained in, for example, Sambrook, 1999, Molecular Cloning: A Laboratory Manual, Second Edition, Cold Spring Harbor Laboratory Press, Cold Spring Harbor, N.Y.; DNA Cloning: A practical Approach, 1985 (D. N. Glover ed); Current Protocols in Molecular Biology, John Wiley & Sons, Inc. (1994) and all more recent editions of these publications.

The following is a discussion of the molecular biology protocol utilized. The described protocols are exemplary in nature and are not meant to limit the scope of the invention.

9.1 Amplification of the Bacterial IMPDH Gene

Bacterial IMPDH DNA was amplified from *E. coli* genomic DNA by PCR using primers 5'-CAGCGGCCG-CAATGCTACGTATCGCTAAAGMGC-3' ("NotI Primer") (SEQ ID NO: 5) and 5'-CCGGATATCGAATCAGGAGC-CCAGACGG-3' ("EcoRV Primer") (SEQ ID NO: 6), which contain flanking NotI and EcoRV restriction endonuclease sites, respectively. The amplification process began by isolating genomic IMPDH DNA from *E. coli* and subsequently amplifying the isolated DNA by PRC.

9.1.1 Isolation of Genomic IMPDH *E. coli* DNA

Isolation of genomic DNA from XL-1 blue *E. coli* bacteria (obtained from GenBank Acession # M10101) was accomplished using the protocol from Julia B. Wolf (University of Maryland, Baltimore County) which she modified from Experimental Techniques in Bacterial Genetics, Jones and Bartlet, 1990. The *E. coli* was grown in a 5 ml bacterial culture overnight. 1.5 ml of the culture was transferred to a microfuge tube, centrifuged for 2 minutes, and the supernatant was decanted. The bacterial pellet was resuspended in 567 μl of TE pH8.0. 30 μl of 10% SDS and 3 μl of 20 mg/ml proteinase K, were added and mixed with the suspended pellet. The mixture was then incubated for 1 hour at 37° C. After incubation the 600 μl of phenol/chloroform was added and the mixture was vortexed, and then centrifuged for 5 minutes. 200 μl of supernatant was transferred to a fresh tube. 40 μl of 3 M sodium acetate was added to the transferred supernatant. 120 μl of isopropanol, was then and mixed by inverting. The DNA was then spooled onto a glass rod. The DNA was then dipped into 70% ethanol to was and was then transferred to a new tube. 1 ml of 70% ethanol was added and to resuspended the DNA and was subsequently centrifuged for 5 minutes. The mixture was then decanted using 70% ethanol, The DNA pellet was air dried and then resuspend in 200 μl of TE pH8.0. The DNA was now ready for use once the concentration of DNA had been determined on a spectrophotometer. The concentration of DNA was determined by measuring the absorbance readings at 260 nm and 280 nm wavelength on a Beckman DU 640 spectrophotometer. (See, Sambrook, 1999). Specifically for measurements of the present samples, the samples were diluted 1:100 in water and the absorbance readings at 260 nm and 280 nm were measured. The ratio of the 260 nm/280 nm values indicates the purity of the DNA sample. For calculating DNA concentration, the 260 nm value was multiplied by 50 (a value of 1 absorbance reading at 260 nm is equal to 50 microgram DNA/ml) and then multiplied by 100 (the dilution factor of the DNA sample). The resultant number is the concentration of DNA in micrograms per ml.

9.1.2 Amplification of MPDH DNA via the Polymerase Chain Reaction "PCR"

The isolated genomic E. coli DNA was subsequently amplified via PCR using a Perkin Elmer DNA thermocycler (Wellesley, Mass.), although other thermocylers could also be used. The following is the list of the PCR mixtures and cycling conditions.

PCR Reaction Mixture

10×Pfu buffer=10 μl

NotI-IMPDHF primer (20 μM)=2 μl

EcoRV-IMPDHR primer (20 μM)=2 μl genomic DNA (800 ng/μl)=0.5 μl

Pfu polymerase (2.5 U/μl)=1 μl dNTP (10 mM)=2 μl ddH2O=82.5 μl

| PCR cycling conditions | |
| --- | --- |
| Step 1: | 95° C. for 3 minutes |
| Step 2: | (30 cycles) |
| | 95° C. for 45 seconds |
| | 60° C. for 45 seconds |
| | 68° C. for 3 minutes |
| Step 3: | 68° C. for 7 minutes |
| Step 4: | 4° C. soak |

An aliquot of the PCR reaction was analyzed on a 0.8% agarose gel for product. Expected size of amplified bacterial IMPDH gene is 1489 bp. Amplified bacterial IMPDH PCR product was cleaned up from the PCR reaction mixture using Qiagen's Qiaquick PCR purification kit.

The sequence of the amplified PCR product (SEQ ID NO: 1) was verified to correspond to bacterial IMPDH by sequencing performed by the company MWG Biotech, Inc (London, England)

The NotI and EcoRV primers were designed by the inventors and sent to MWG Biotech for oligonucleotide synthesis using their proprietary synthesis method.

9.2 Construction of pFLAG-IMPDH Plasmid

The PCR fragment resulting from the above protocols was ligated into the pFLAG-CMV-2 vector (Sigma, St. Louis, Mo.) to generate the plasmid pFLAG-IMPDH (FIG. 1A) using the following protocol:

9.2.1 Preparation of the IMPDH PCR Product

The IMPDH PCR product was digested with the enzymes NotI and EcoRV. The digested IMPDH PCR product was then cleaned up using Qiagen's Qiaquick PCR purification kit.

9.2.2 Preparation of the pFLAG-CMV2 Plasmid Vector

The pFLAG-CMV2 plasmid vector purchased from (Sigma, St. Louis, Mo.) was digested with the enzymes NotI and EcoRV. The digested pFLAG-CMV2 plasmid vector was then cleaned up using Qiagen's Qiaquick PCR purification kit.

9.2.3 Ligation of the IMPDH PCR Product to the pFLAG-CMV2 Plasmid Vector

A 1:10 ratio of pFLAG-CMV2 plasmid vector to IMPDH PCR product was used for the ligation reaction, using 100 ng total DNA per ligation. The ligation reaction set up was as follows:

10× ligation buffer=1 μl

Digested IMPDH PCR product (13.5 ng/μl)=5.6 μl

Digested pFLAG-CMV2 vector (15 ng/μl)=1.7 μl

T4 DNA ligase (10 Units/μl)=1 μl ddH2O=0.7 μl

The ligation reaction was incubated overnight (18 hours) at room temperature.

9.2.4 Transformation of the Ligation Reaction into Bacteria

3 μl (30 ng of DNA) of the ligation reaction was added to 100 μl of competent cells in an eppendorf tube (type of cells). The cells were incubated on ice for 30 minutes, heat-shocked for 45 seconds at 37° C. and placed back on ice for 2 minutes. The cells were then transferred to a tube containing 0.9 ml of LB broth and incubated for 1 hour at 37° C. in a shaking incubator. The cells (100 μl) were then spread out on LB agar plates containing 50 μg/ml ampicillin and were incubated overnight at 37° C. until growth of bacterial colonies was visible.

9.3 Testing Bacteria Colonies for Plasmid Containing pFLAG-IMPDH

The bacterial colonies were than tested for the presence of the pFLAG-IMPDH plasmid. Bacterial colonies were picked and transferred to 5 ml of LB broth containing 50 μg/ml ampicillin. The bacterial cultures were incubated overnight at 37° C. in a shaking incubator. After incubation, 1.5 ml of bacterial cultures was transferred to eppendorf tubes and centrifuged for 2 minutes. Supernatants were discarded and bacterial plasmids were isolated using Qiagen's Qiaprep Spin Miniprep kit. Plasmid DNA was subjected to various restriction endonuclease digestions and DNA was separated on a 0.8% agarose gel to confirm the presence of plasmid DNA and the IMPDH gene.

9.4 Construction of pIMPDH-EGFP Expression Vector

A bicistronic expression vector containing FLAG-tagged bacterial IMPDH and EGFP (pIMPDH-EGFP, FIG. 1B) was constructed after excising the IMPDH DNA fragment from the pFLAG-IMPDH plasmid and ligating it into the pIRES2-EGFP vector (BD Biosciences Clontech, Palo Alto, Calif.) using the following protocols.

9.4.1 Preparation of the FLAG-IMPDH DNA Fragment

The pFLAG-IMPDH plasmid was digested with NdeI and SalI endonucleases. The digested DNA was then separated on a 0.8% agarose gel which yielded two DNA fragments: 4249 bp and 1887 bp. The 1887 bp fragment which contains the IMPDH gene was purified from the agarose gel using Qiagen's Qiaquick gel extraction kit.

9.4.2 Preparation of the pIRES2-EGFP Plasmid Vector

The pIRES2-EGFP plasmid vector was digested with NdeI and SalI endonucleases. Digested DNA was separated on a 0.8% agarose gel. Digestion of DNA yielded two DNA fragments: 4903 bp and 405 bp. The 4903 bp fragment was purified from the agarose gel using Qiagen's Qiaquick gel extraction kit.

9.4.3 Ligation of the FLAG-IMPDH DNA Fragment to the pIRES2-EGFP Plasmid Vector A 1:10 ratio of pIRES2-EGFP plasmid vector to IMPDH DNA fragment was used for the ligation reaction, using 100 ng total DNA per ligation. The ligation reaction setup was a follows:

10× ligation buffer=1 µl 1887 bp IMPDH DNA fragment (16.5 ng/µl)=4 µl 4903 bp pIRES2-EGFP DNA fragment (34 ng/µl)=1 µl T4 DNA ligase (10 Units/µl)=1 µl ddH2O=3 µl The ligation reaction was incubated overnight (18 hours) at room temperature.

9.4.4 Transformation of the Ligation Reaction into Bacteria

3 µl (30 ng of DNA) of the ligation reaction was added to 100 µl of competent cells in an eppendorf tube. Cells were incubated on ice for 30 minutes and then heat-shocked for 45 seconds at 37° C. The Cells were placed back on ice for 2 minutes, transferred to a tube containing 0.9 ml of LB broth and incubated for 1 hour at 37° C. in a shaking incubator. Cells (100 µl) were then spread out on LB agar plates containing 30 µg/ml kanamycin and incubated overnight at 37° C. until growth of bacterial colonies was visible.

9.5 Testing Bacteria Colonies for Plasmid Containing pIMPDH-EGFP

Bacterial colonies were picked and transferred to 5 ml of LB broth containing 30 µg/ml kanamycin. The bacterial cultures were incubated overnight at 37° C. in a shaking incubator. 1.5 ml of bacterial cultures were transferred to eppendorf tubes and centrifuged for 2 minutes. Supernatants were discarded and bacterial plasmids were isolated using Qiagen's Qiaprep Spin Miniprep kit. Plasmid DNA was subjected to various restriction endonuclease digestions and DNA was separated on an agarose gel to confirm the presence of plasmid DNA and the IMPDH gene

9.6 Construction of pNEO-EGFP Expression Vector

A bicistronic expression vector containing the neo and EGFP genes (pNEO-EGFP, FIG. 1C) was constructed after PCR amplifying the neo gene from the pCDNA3 vector and ligating it into the pIRES2-EGFP vector using the following protocols. The constitutively expressing EGFP vector (pHygEGFP) was purchased from BD Biosciences Clontech (Palo Alto, Calif.).

9.6.1 Preparation of the NEO Gene

PCR primers for amplification of the NEO gene were designed by inventors and sent to MWG Biotech for oligonucleotide synthesis using their proprietary synthesis method. The primers are: SstINeoF (5'-gccgagctccgcatgat-tgaacaagatgg-3') (SEQ ID NO: 7) and EcoRINeoR (5'-ccggaattcagctcagaagaactcgtcaag-3') (SEQ ID NO: 8). The primers SstINeoF and EcoRINeoR primers contain part of the neomycin resistant gene sequence and sequences for the restriction endonucleases SstI and EcoRI, respectively. The NEO gene was amplified using the plasmid vector pCDNA3 (Invitrogen) as the source of the neo gene template.

9.6.2 Amplification of Neo Gene via PCR

The Neo DNA was subsequently amplified via PCR using a Perkin Elmer DNA thermocycler (Wellesley, Mass.), although other thermocylers could also be used. The following is the list of the PCR mixtures and cycling conditions.

PCR Reaction Mixture

10×Pfu buffer=10 µl

SstINeoF primer (10 µM)=5 µl

EcoRINeoR primer (10 µM)=5 µl pCDNA3 plasmid (74.5 ng/µl)=1.3 µl

Pfu polymerase (2.5 Units/µl)=1 µl dNTP (10 mM)=2 µl ddH2O=75.7 µl

| PCR cycling conditions | |
| --- | --- |
| Step 1: | 95° C. for 3 minutes |
| Step 2: | (30 cycles) |
|  | 95° C. for 45 seconds |
|  | 60° C. for 45 seconds |
|  | 68° C. for 2 minutes |
| Step 3: | 68° C. for 7 minutes |
| Step 4: | 4° C. soak |

An aliquot of the PCR reaction was analyzed on a 0.8% agarose gel for product. Expected size of amplified NEO gene DNA fragment is 818 bp. The amplified NEO gene PCR product was cleaned up from the PCR reaction mixture using Qiagen's Qiaquick PCR purification kit. The NEO gene PCR product was then digested with the enzymes SstI and EcoRI. The digested NEO gene PCR product was then cleaned up using Qiagen's Qiaquick PCR purification kit.

9.6.3 Preparation of the pIRES-EGFP Plasmid Vector

The pIRES-EGFP plasmid vector was digested with the enzymes SstI and EcoRI. The digested pIRES-EGFP plasmid vector was then cleaned up using Qiagen's Qiaquick PCR purification kit.

9.6.4 Ligation of the NEO Gene PCR Product into the pIRES-EGFP Plasmid Vector A 1:10 ratio of pIRES-EGFP plasmid vector to NEO gene PCR product was used for the ligation reaction, using 100 ng total DNA per ligation. The following described the ligation reaction setup.

10× ligation buffer=1 μl

Digested NEO gene PCR product (30 ng/μl)=2 μl

Digested pIRES-EGFP vector (36.5 ng/μl)=1.1 μl

T4 DNA ligase (10 Units/μl)=1 μl ddH2O=4.9 μl

The ligation reaction was incubated overnight (18 hours) at room temperature.

9.6.5 Transformation of the Ligation Reaction into Bacteria 3 ul (30 ng of DNA) of the ligation reaction was then added to 100 μl competent cells in an eppendorf tube. The cells were incubated on ice for 30 minutes and then heat-shocked for 45 seconds at 37° C. Cells were placed back on ice for 2 minutes, then transferred to a tube containing 0.9 ml of LB broth and incubated for 1 hour at 37° C. in a shaking incubator. Cells (100 μl) were then spread out on LB agar plates containing 30 μg/ml kanamycin. Plates were incubated overnight at 37° C. until growth of bacterial colonies was visible.

9.7 Testing Bacteria Colonies for Plasmid Containing pNEO-EGFP

Bacterial colonies were picked and transferred to 5 ml of LB broth containing 30 μg/ml kanamycin and incubated overnight at 37° C. in a shaking incubator. 1.5 ml of bacterial cultures were transferred to eppendorf tubes and centrifuged for 2 minutes.

Supernatants were discarded and bacterial plasmids were isolated using Qiagen's Qiaprep Spin Miniprep kit. Plasmid DNA was subjected to various restriction endonuclease digestions and DNA was separated on a 0.8% agarose gel to confirm the presence of plasmid DNA and the NEO gene.

9.8 Mammalian Cell Transfection

The mammalian cells ($2 \times 10^7$) (i.e. V79, MDA-MB-231, PC3, COS7) were washed once with phosphate buffered saline (PBS), resuspended in 400 μl of Cytomix buffer, placed in an electroporation cuvette and transfected with 10 μg of DNA by electroporation at 200V, 30 ms, in an ElectroSquarePorator T280 electroporator (BTX, Inc., San Diego, Calif.). Immediately after electroporation, the cuvettes were placed on ice for 10–15 min. After that the cells were washed once in PBS and $1 \times 10^6$ viable cells, as determined by trypan blue exclusion, were re-suspended in 10 ml of growth medium in 100 mm tissue culture plates, incubated overnight at 37° C. and treated the next day with 0.8 μg/ml of MPA (stock concentration at 14.2 mg/ml in DMSO, Sigma, St. Louis, Mo.) or 600 μg/ml of G418. For the different assays, cells were obtained from either individual or pooled MPA-resistant colonies. For colony isolation, visible individual colonies were each picked and aspirated into a glass Pasteur pipette and transferred into a well of a 24-well tissue culture plate. The next day, after rinsing the wells with the colonies with PBS and incubation for 1–2 min in a drop of a trypsin/EDTA solution, the cells within each well were dispersed by forceful pipetting. Next, the cells were incubated in growth medium to generate a monolayer culture, which was used to determine the cells' susceptibility to MPA. Cultures were also obtained from single MPA-resistant cells derived from pooled colonies by seeding 2.5 cells/ml into 96-well flat-bottom microtiter plates in 200 μl of growth medium/well and only cultures deriving from wells that were initially found to contain single cells were used. MPA toxicity was determined by the MTT (methylthiazoletetrazolium) assay (described in detail below) while the expression of the green fluorescent protein (GFP) was detected by fluorescence microscopy and/or flow cytometry.

9.9 Mammalian Cell Lines

All cell lines used were obtained from the American Type Culture Collection (Manassas, Va.) ("ATCC"). They are V79 (Chinese hamster lung tissue cell line, ATCC# CCL-93), MDA-MB-321 (human breast, mammary gland, epithelial pleural effusion adenocarcinoma, ATCC# HTB-26), PC-3 (human prostatic adenocarcinoma from a bone metastatic site, ATCC# CRL-1435), and COS-7 (African green monkey, SV40-transformed, kidney cell line, ATCC# CRL-1651).

9.10 Cell Growth Mediums for Mammalian Cell Lines

Growth medium for growing all of the cell lines is RPMI 1640 medium supplemented with 10% heat-inactivated FBS (fetal bovine serum), 2 mM L-glutamine, 100 Units/ml penicillin, and 100 μl/ml strex ptomycin. To obtain sufficient numbers of cells ($2 \times 10^7$ cells) for transfection, cells were seeded on 100×20 mm tissue culture dishes and allowed to grow, forming a confluent monolayer on the dishes. The cells were harvested by detachment from the dishes using a solution of trypsin/EDTA followed by transferring of detached cells to 15 ml conical tubes and washed 2 times with RPMI-1640. Cells were counted using a hemacytometer and trypan blue exclusion and an appropriated number of cells were used for transfection.

9.11 Supplemented Cell Growth Medium for IMPDH-Transfected Mammalian Cell Lines For cells transfected with an IMPDH-containing plasmid, cells were grown in growth medium (described in section 5a above) supplemented with 0.8 μg/ml of MPA. The growth medium for cells transfected with the pNEO-EGFP plasmid contains 600 μg/ml of G418. The specific procedure for growth of the cells post-transfection are as follows: After transfection by electroporation the electroporation cuvette was place on ice for 10–15 minutes. Cells were washed once in PBS and cell viability was determined using a hemacytometer and trypan blue exclusion. $1\times10^6$ viable cells were resuspended in 10 ml of growth medium in 100×20 mm tissue culture dishes and incubated at 37° C. in a $CO_2$ incubator overnight. The next day MPA (final concentration of 0.8 µg/ml) was added to the dishes. For the pNEO-EGFP transfectants, G418 (final concentration of 600 µg/ml) was added to the dishes. Transfectants were incubated at 37° C. in a $CO_2$ incubator for 2–4 weeks until growth positive colonies were visible on the dishes. Individual colonies were pipetted into separated tissue culture dishes and expanded in growth medium supplemented with MPA or G418. For additional subcloning of transfectants, 96-well flat bottom microtiter plates were seeded with 200 µl per well of a 2.5 cells/ml suspension of a given transfectant. Wells that contain one cell were identified, expanded, and used for experiments.

9.12 MTT Assay

Cell survival and proliferation was measured using the MTT assay, which detects active mitochondria and as a result viable cells. For this assay, $2\times10^4$ cells were suspended in 200 µl of growth medium/well in 96-well flat-bottom microtiter plates with various stimuli and incubated at 37° C. After 6 d, 10 µl of MTT solution (5 mg/ml in PBS) (Sigma, St. Louis, Mo.) was added to each well and the plates were incubated for an additional 4 h at 37° C. In the case of V79 cells, which grow twice as fast as the other cell lines, the MTT solution was added after 3 d. The plates were then centrifuged at 1000 rpm for 5 min, supernatants discarded and 100 µl of DMSO added per well, and the plates were read at 540 nm using a microtiter plate reader.

9.13 Western Blotting

Cells ($2\times10^6$) were lysed in 100 µl of boiling 2×SDS-PAGE sample dye for 15 min after which time 10 µl of lysate samples were subjected to SDS-PAGE and electroblotted to Hybond-C extra nitrocellulose membrane (Amersham Biosciences, Piscataway, N.J.). The FLAG epitope-tagged *E. coli* IMPDH was visualized with an anti-FLAG (M2) antibody (Sigma, St. Louis, Mo.) and goat anti-mouse IgG-HRP (BioRad, Hercules, Calif.) using enhanced chemiluminescence (Pierce, Rockford, Ill.).

Having described the basic concept of the invention, it will be apparent to those skilled in the art that the foregoing detailed disclosure is intended to be presented by way of example only, and is not limiting. Various alterations, improvements, and modifications are intended to be suggested and are within the scope and spirit of the present invention. Additionally, the recited order of the elements or sequences, or the use of numbers, letters or other designations therefore, is not intended to limit the claimed processes to any order except as may be specified in the claims. Accordingly, the invention is limited only by the following claims and equivalents thereto.

All publications and patent documents cited in this application are incorporated by reference in their entirety for all purposes to the same extent as if each individual publication or patent document were so individually denoted.

---

We claim:

1. A eukaryotic expression vector comprising the bacterial Inosine 5'-monophosphate dehydrogenase (IMPDH) nucleic acid sequence wherein:
    said IMPDH nucleic acid sequence is operably linked to at least one transcription regulatory sequence to confer expression of said bacterial IMPDH by a eukaryotic host upon transfection with said expression vector; and
    wherein the bacterial IMPDH nucleic acid sequence is a nucleic acid sequence selected from the group of nucleic acid sequences consisting of:
        a nucleic acid sequence at least 95% identical to SEQ ID NO: 1;
        a nucleic acid sequence that encodes a sequence of amino acids comprising SEQ ID NO: 2; and
        a nucleic acid sequence that encodes a polypeptide having a sequence at least 95% identical to SEQ ID NO. 2.

2. A eukaryotic expression vector comprising the bacterial Inosine 5'-monophosphate dehydrogenase (IMPDH) nucleic acid sequence wherein:
    said IMPDH nucleic acid sequence is operably linked to at least one transcription regulatory sequence to confer expression of said bacterial IMPDH by a eukaryotic host upon transfection with said expression vector; and
    wherein the bacterial IMPDH nucleic acid sequence comprises SEQ ID NO: 1 or a degenerate variant of SEQ ID NO: 1.

3. The eukaryotic expression vector of claim 1, wherein the bacterial IMPDH nucleic acid sequence comprises a sequence at least 95% identical to SEQ ID NO: 1.

4. A eukaryotic expression vector comprising the bacterial Inosine 5'-monophosphate dehydrogenase (IMPDH) nucleic acid sequence wherein:
    said IMPDH nucleic acid sequence is operably linked to at least one transcription regulatory sequence to confer expression of said bacterial IMPDH by a eukaryotic host upon transfection with said expression vector; and
    wherein the bacterial IMPDH nucleic acid sequence comprises a sequence at least 95% identical to SEQ ID NO: 1.

5. The eukaryotic expression vector of claim 1, wherein the bacterial IMPDH nucleic acid sequence comprises a sequence that encodes a sequence of amino acids comprising SEQ ID NO: 2.

6. The eukaryotic expression vector of claim 1, wherein the bacterial IMPDH nucleic acid sequence comprises a sequence that encodes a polypeptide having a sequence at least 95% identical to SEQ ID NO. 2.

7. A eukaryotic expression vector comprising the bacterial Inosine 5'-monophosphate dehydrogenase (IMPDH) nucleic acid sequence wherein:
    said IMPDH nucleic acid sequence is operably linked to at least one transcription regulatory sequence to confer expression of said bacterial IMPDH by a eukaryotic host upon transfection with said expression vector; and
    the bacterial IMPDH nucleic acid sequence comprises a sequence that encodes a polypeptide having a sequence at least 95% identical to SEQ ID NO: 2.

8. The eukaryotic expression vector of claim 2, wherein the eukaryotic host cell is a mammalian cell which is resistant to mycophenolic acid "MPA", or an analog of MPA, upon expression of said bacterial IMPDH.

9. The eukaryotic expression vector of claim 2, further comprising at least one additional nucleic acid sequence expressible in a mammalian cell.

10. The eukaryotic expression vector of claim 9, wherein at least one additional nucleic acid sequence is a dominant selectable marker.

11. The eukaryotic expression vector of claim 2, wherein the expression vector is a eukaryotic expression vector selected from the group consisting of: pCI, pSI pRK-5-C-GFP, pRK-5-N-GFP, Vitality hrGFPII-1, LRCX retroviral vectors, pTracer-CMV-2 vector, pCDNA, pCEP4 episomal mammalian expression vector, and pDisplay vector.

12. The eukaryotic expression vector of claim 4, wherein the eukaryotic host cell is a mammalian cell which is resistant to mycophenolic acid "MPA", or an analog of MPDA, upon expression of said bacterial IMPDH.

13. The eukaryotic expression vector of claim 4, further comprising at least one additional nucleic acid sequence expressible in a mammalian cell.

14. The eukaryotic expression vector of claim 13, wherein at least one additional nucleic acid sequence is a dominant selectable marker.

15. The eukaryotic expression vector of claim 4, wherein the expression vector is a eukaryotic expression vector selected from the group consisting of: pCI, pSI pRK-5-C-GFP, pRK-5-N-GFP, Vitality hrGFPII-1, LRCX retroviral vectors, pTracer-CMV-2 vector, pCDNA, pCEP4 episomal mammalian expression vector, and pDisplay vector.

16. The eukaryotic expression vector of claim 7, wherein the eukaryotic host cell is a mammalian cell which is resistant to mycophenolic acid "MPA", or an analog of MPDA, upon expression of said bacterial IMPDH.

17. The eukaryotic expression vector of claim 7, further comprising at least one additional nucleic acid sequence expressible in a mammalian cell.

18. The eukaryotic expression vector of claim 17, wherein at least one additional nucleic acid sequence is a dominant selectable marker.

19. The eukaryotic expression vector of claim 7, wherein the expression vector is a eukaryotic expression vector selected from the group consisting of: pCI, pSI pRK-5-C-GFP, pRK-5-N-GFP, Vitality hrGFPII-1, LRCX retroviral vectors, pTracer-CMV-2 vector, pCDNA, pCEP4 episomal mammalian expression vector, and pDisplay vector.

* * * * *

SEQUENCE LISTING

<160> NUMBER OF SEQ ID NOS: 8

<210> SEQ ID NO 1
<211> LENGTH: 1506
<212> TYPE: DNA
<213> ORGANISM: Artificial
<220> FEATURE:
<223> OTHER INFORMATION: isolated E.coli IMPDH cDNA

<400> SEQUENCE: 1

```
atggactaca aagacgatga cgacaagctt gcggccgcaa tgctacgtat cgctaaagaa      60
gctctgacgt tgacgacgt tctcctcgtt cctgctcact ctaccgttct gccgaatact     120
gctgacctca gcacccagct gacgaaaact attcgtctga atatccctat gctttccgca    180
gcaatggata ccgtaacgga agcgcgcctg gctattgctc tggctcagga aggcggtatc    240
ggctttatcc acaaaaacat gtccattgaa cgccaggcag aagaagttcg ccgtgtgaaa    300
aaacacgaat ctggtgtggt gactgatccg cagactgttc tgccaaccac gacgctgcgc    360
gaagtgaaag aactgaccga gcgtaacggt tttgcgggct atccggtcgt taccgaagaa    420
aacgaactgg tgggtattat caccggtcgt gacgtgcgtt ttgttaccga cctgaaccag    480
ccggttagcg tttacatgac gccgaaagag cgtctggtca ccgtgcgtga aggtgaagcc    540
cgtgaagtgg tgctggcaaa aatgcacgaa aaacgcgttg aaaaagcgct ggtggttgat    600
gacgaattcc acctgatcgg catgatcacc gtgaaagact ccagaaagc ggaacgtaaa    660 ccgaacgcct gtaaagacga gcaaggccgt ctgcgtgttg gtgcagcggt tggcgcaggt    720
```

-continued

```
gcgggtaacg aagagcgtgt tgacgcgctg gttgccgcag gcgttgacgt tctgctgatc    780
gactcctccc acggtcactc agaaggtgta ctgcaacgta tccgtgaaac ccgtgctaaa    840
tatccggatc tgcaaattat cggcggcaac gtggcaacag ctgcaggtgc acgcgctctg    900
gcagaagctg gttgcagtgc ggttaaagtc ggcattggcc ctggctctat ctgtacaact    960
cgtatcgtga ctggcgtcgg tgttccgcag attaccgctg ttgctgacgc agtagaagcc   1020
ctggaaggca ccggtattcc ggttatcgct gatggcggta ttcgcttctc cggcgacatc   1080
gccaaagcta tcgccgctgg cgcaagcgcg gtgatggtag gttccatgct ggcgggtact   1140
gaagaatctc cgggtgaaat cgaactctac cagggccgtt cttacaaatc ttaccgtggt   1200
atgggttccc tgggcgcgat gtccaaaggt tcctctgacc gttatttcca gagcgataac   1260
gctgccgaca aactggtgcc ggaaggtatc gaaggtcgcg tagcctataa aggtcgcctg   1320
aaagagatca ttcaccagca gatgggcggc ctgcgctcct gtatgggtct gaccggctgt   1380
ggtactatcg acgaactgcg tactaaagcg gagtttgtac gtatcagcgg tgcgggcatt   1440
caggaaagcc acgttcacga cgtgaccatt actaaagagt ccccgaacta ccgtctgggc   1500
tcctga                                                             1506
```

<210> SEQ ID NO 2
<211> LENGTH: 501
<212> TYPE: PRT
<213> ORGANISM: Artificial
<220> FEATURE:
<223> OTHER INFORMATION: isolated E.coli IMPDH protein sequence

<400> SEQUENCE: 2

```
Met Asp Tyr Lys Asp Asp Asp Lys Leu Ala Ala Ala Met Leu Arg
1               5                   10                  15

Ile Ala Lys Glu Ala Leu Thr Phe Asp Asp Val Leu Leu Val Pro Ala
            20                  25                  30

His Ser Thr Val Leu Pro Asn Thr Ala Asp Leu Ser Thr Gln Leu Thr
        35                  40                  45

Lys Thr Ile Arg Leu Asn Ile Pro Met Leu Ser Ala Ala Met Asp Thr
    50                  55                  60

Val Thr Glu Ala Arg Leu Ala Ile Ala Leu Ala Gln Glu Gly Gly Ile
65                  70                  75                  80

Gly Phe Ile His Lys Asn Met Ser Ile Glu Arg Gln Ala Glu Glu Val
                85                  90                  95

Arg Arg Val Lys Lys His Glu Ser Gly Val Val Thr Asp Pro Gln Thr
            100                 105                 110

Val Leu Pro Thr Thr Thr Leu Arg Glu Val Lys Glu Leu Thr Glu Arg
        115                 120                 125

Asn Gly Phe Ala Gly Tyr Pro Val Val Thr Glu Glu Asn Glu Leu Val
    130                 135                 140

Gly Ile Ile Thr Gly Arg Asp Val Arg Phe Val Thr Asp Leu Asn Gln
145                 150                 155                 160

Pro Val Ser Val Tyr Met Thr Pro Lys Glu Arg Leu Val Thr Val Arg
                165                 170                 175

Glu Gly Glu Ala Arg Glu Val Val Leu Ala Lys Met His Glu Lys Arg
            180                 185                 190

Val Glu Lys Ala Leu Val Val Asp Asp Glu Phe His Leu Ile Gly Met
        195                 200                 205

Ile Thr Val Lys Asp Phe Gln Lys Ala Glu Arg Lys Pro Asn Ala Cys
    210                 215                 220
```

```
Lys Asp Glu Gln Gly Arg Leu Arg Val Gly Ala Ala Val Gly Ala Gly
225                 230                 235                 240

Ala Gly Asn Glu Glu Arg Val Asp Ala Leu Val Ala Ala Gly Val Asp
            245                 250                 255

Val Leu Leu Ile Asp Ser Ser His Gly His Ser Glu Gly Val Leu Gln
            260                 265                 270

Arg Ile Arg Glu Thr Arg Ala Lys Tyr Pro Asp Leu Gln Ile Ile Gly
            275                 280                 285

Gly Asn Val Ala Thr Ala Ala Gly Ala Arg Ala Leu Ala Glu Ala Gly
290                 295                 300

Cys Ser Ala Val Lys Val Gly Ile Gly Pro Gly Ser Ile Cys Thr Thr
305                 310                 315                 320

Arg Ile Val Thr Gly Val Gly Val Pro Gln Ile Thr Ala Val Ala Asp
            325                 330                 335

Ala Val Glu Ala Leu Glu Gly Thr Gly Ile Pro Val Ile Ala Asp Gly
            340                 345                 350

Gly Ile Arg Phe Ser Gly Asp Ile Ala Lys Ala Ile Ala Ala Gly Ala
            355                 360                 365

Ser Ala Val Met Val Gly Ser Met Leu Ala Gly Thr Glu Glu Ser Pro
370                 375                 380

Gly Glu Ile Glu Leu Tyr Gln Gly Arg Ser Tyr Lys Ser Tyr Arg Gly
385                 390                 395                 400

Met Gly Ser Leu Gly Ala Met Ser Lys Gly Ser Ser Asp Arg Tyr Phe
            405                 410                 415

Gln Ser Asp Asn Ala Ala Asp Lys Leu Val Pro Glu Gly Ile Glu Gly
            420                 425                 430

Arg Val Ala Tyr Lys Gly Arg Leu Lys Glu Ile Ile His Gln Gln Met
            435                 440                 445

Gly Gly Leu Arg Ser Cys Met Gly Leu Thr Gly Cys Gly Thr Ile Asp
450                 455                 460

Glu Leu Arg Thr Lys Ala Glu Phe Val Arg Ile Ser Gly Ala Gly Ile
465                 470                 475                 480

Gln Glu Ser His Val His Asp Val Thr Ile Thr Lys Glu Ser Pro Asn
            485                 490                 495

Tyr Arg Leu Gly Ser
            500

<210> SEQ ID NO 3
<211> LENGTH: 1466
<212> TYPE: DNA
<213> ORGANISM: Escherichia coli

<400> SEQUENCE: 3
atgctacgta tcgctaaaga agctctgacg tttgacgacg ttctcctcgt tcctgctcac    60
tctaccgttc tgccgaatac tgctgacctc agcacccagc tgacgaaaac tattcgtctg   120
aatatcccta tgctttccgc agcaatggat accgtaacgg aagcgcgcct ggctattgct   180
ctggctcagg aaggcggtat cggctttatc cacaaaaaca tgtccattga cgccaggca    240 gaagaagttc gccgtgtgaa aaaacacgaa tctggtgtgg tgactgatcc gcagactgtt   300
ctgccaacca cgacgctgcg cgaagtgaaa gaactgaccg agcgtaacgg ttttgcgggc   360
tatccggtcg ttaccgaaga aaacgaactg tgggtattta tcaccggtcg tgacgtgcgt   420
tttgttaccg acctgaacca gccggttagc gtttacatga cgccgaaaga gcgtctggtc   480
```

-continued

```
accgtgcgtg aaggtgaagc ccgtgaagtg gtgctggcaa aaatgcacga aaaacgcgtt      540
gaaaaagcgc tggtggttga tgacgaattc cacctgatcg gcatgatcac cgtgaaagac      600
ttccagaaag cggaagctaa accgaacgcc tgtaaagacg agcaaggccg tctgcgtgtt      660
ggtgcagcgg ttgcgcaggt gcgggtaac gaagagcgtg ttgacgcgct ggttgccgca       720
ggcgttgacg ttctgctgat cgactcctcc cacggtcact cagaaggtgt actgcaacgt      780
atccgtgaaa cccgtgctaa atatccggat ctgcaaatta tcggcggcaa cgtggcaaca      840
gctgcaggtg cacgcgctct ggcagaagct ggttgcagtg cggttaaagt cggcattggc      900
cctggctcta tctgtacaac tcgtatcgtg actggcgtcg tgttccgca gattaccgct       960
gttgctgacg cagtagaagc cctggaaggc accggtattc cggttatcgc tgatggcggt     1020
attgcttct ccggcgacat cgccaaagct atcgccgctg cgcaagcgc ggtgatggta       1080
ggttccatgc tggcgggtac tgaagaatct ccgggtgaaa tcgaactcta ccagggccgt     1140
tcttacaaat cttaccgtgg tatgggttcc ctgggcgcga tgtccaaagg ttcctctgac     1200
cgttatttcc agagcgataa cgctgccgac aaactggtgc cggaaggtat cgaaggtcgc     1260
gtagcctata aaggtcgcct gaaagagatc attcaccagc agatgggcgg cctgcgctcc     1320
tgtatgggtc tgaccggctg tggtactatc gacgaactgc gtactaaagc ggagtttgta     1380
cgtatcagcg gtgcgggcat tcaggaaagc cacgttcaca cgtgaccatt actaaagagt     1440
ccccgaacta ccgtctgggc tcctga                                          1466
```

```
<210> SEQ ID NO 4
<211> LENGTH: 488
<212> TYPE: PRT
<213> ORGANISM: Escherichia coli
<220> FEATURE:
<221> NAME/KEY: misc_feature
<222> LOCATION: (488)..(488)
<223> OTHER INFORMATION: Xaa can be any naturally occurring amino acid

<400> SEQUENCE: 4
```

Met Leu Arg Ile Ala Lys Glu Ala Leu Thr Phe Asp Asp Val Leu Leu
1               5                   10                  15

Val Pro Ala His Ser Thr Val Leu Pro Asn Thr Ala Asp Leu Ser Thr
            20                  25                  30

Gln Leu Thr Lys Thr Ile Arg Leu Asn Ile Pro Met Leu Ser Ala Ala
        35                  40                  45

Met Asp Thr Val Thr Glu Ala Arg Leu Ala Ile Ala Leu Ala Gln Glu
    50                  55                  60

Gly Gly Ile Gly Phe Ile His Lys Asn Met Ser Ile Glu Arg Gln Ala
65                  70                  75                  80

Glu Glu Val Arg Arg Val Lys Lys His Glu Ser Gly Val Val Thr Asp
                85                  90                  95

Pro Gln Thr Val Leu Pro Thr Thr Leu Arg Glu Val Lys Glu Leu
            100                 105                 110

Thr Glu Arg Asn Gly Phe Ala Gly Tyr Pro Val Val Thr Glu Glu Asn
        115                 120                 125

Glu Leu Val Gly Ile Ile Thr Gly Arg Asp Val Arg Phe Val Thr Asp
    130                 135                 140

Leu Asn Gln Pro Val Ser Val Tyr Met Thr Pro Lys Glu Arg Leu Val
145                 150                 155                 160

Thr Val Arg Glu Gly Glu Ala Arg Glu Val Val Leu Ala Lys Met His
                165                 170                 175

-continued

```
Glu Lys Arg Val Glu Lys Ala Leu Val Val Asp Asp Glu Phe His Leu
            180                 185                 190
Ile Gly Met Ile Thr Val Lys Asp Phe Gln Lys Ala Glu Ala Lys Pro
            195                 200                 205
Asn Ala Cys Lys Asp Glu Gln Gly Arg Leu Arg Val Gly Ala Ala Val
            210                 215                 220
Gly Ala Gly Ala Gly Asn Glu Glu Arg Val Asp Ala Leu Val Ala Ala
225                 230                 235                 240
Gly Val Asp Val Leu Leu Ile Asp Ser Ser His Gly His Ser Glu Gly
                245                 250                 255
Val Leu Gln Arg Ile Arg Glu Thr Arg Ala Lys Tyr Pro Asp Leu Gln
            260                 265                 270
Ile Ile Gly Gly Asn Val Ala Thr Ala Ala Gly Ala Arg Ala Leu Ala
            275                 280                 285
Glu Ala Gly Cys Ser Ala Val Lys Val Gly Ile Gly Pro Gly Ser Ile
            290                 295                 300
Cys Thr Thr Arg Ile Val Thr Gly Val Gly Val Pro Gln Ile Thr Ala
305                 310                 315                 320
Val Ala Asp Ala Val Glu Ala Leu Glu Gly Thr Gly Ile Pro Val Ile
                325                 330                 335
Ala Asp Gly Gly Ile Arg Phe Ser Gly Asp Ile Ala Lys Ala Ile Ala
            340                 345                 350
Ala Gly Ala Ser Ala Val Met Val Gly Ser Met Leu Ala Gly Thr Glu
            355                 360                 365
Glu Ser Pro Gly Glu Ile Glu Leu Tyr Gln Gly Arg Ser Tyr Lys Ser
            370                 375                 380
Tyr Arg Gly Met Gly Ser Leu Gly Ala Met Ser Lys Gly Ser Ser Asp
385                 390                 395                 400
Arg Tyr Phe Gln Ser Asp Asn Ala Ala Asp Lys Leu Val Pro Glu Gly
                405                 410                 415
Ile Glu Gly Arg Val Ala Tyr Lys Gly Arg Leu Lys Glu Ile Ile His
            420                 425                 430
Gln Gln Met Gly Gly Leu Arg Ser Cys Met Gly Leu Thr Gly Cys Gly
            435                 440                 445
Thr Ile Asp Glu Leu Arg Thr Lys Ala Glu Phe Val Arg Ile Ser Gly
450                 455                 460
Ala Gly Ile Gln Glu Ser His Val His Thr Pro Leu Leu Lys Ser Pro
465                 470                 475                 480
Arg Thr Thr Val Trp Ala Pro Xaa
                485
```

<210> SEQ ID NO 5
<211> LENGTH: 34
<212> TYPE: DNA
<213> ORGANISM: Artificial
<220> FEATURE:
<223> OTHER INFORMATION: NotI-IMPDHPrimer-F

<400> SEQUENCE: 5
cagcggccgc aatgctacgt atcgctaaag aagc        34

<210> SEQ ID NO 6
<211> LENGTH: 28
<212> TYPE: DNA
<213> ORGANISM: Artificial
<220> FEATURE:
<223> OTHER INFORMATION: EcoRV-IMPDH-Primer-R

```
<400> SEQUENCE: 6
ccggatatcg aatcaggagc ccagacgg                                           28

<210> SEQ ID NO 7
<211> LENGTH: 29
<212> TYPE: DNA
<213> ORGANISM: Artificial
<220> FEATURE:
<223> OTHER INFORMATION: SstINeo-Primer-F

<400> SEQUENCE: 7
gccgagctcc gcatgattga acaagatgg                                          29

<210> SEQ ID NO 8
<211> LENGTH: 30
<212> TYPE: DNA
<213> ORGANISM: Artificial
<220> FEATURE:
<223> OTHER INFORMATION: EcoRI-Neo-Primer-R

<400> SEQUENCE: 8
ccggaattca gctcagaaga actcgtcaag                                         30
```